(12) United States Patent  
Liphardt et al.

(10) Patent No.: US 8,339,602 B1  
(45) Date of Patent: Dec. 25, 2012

(54) VIEW-FINDER IN ELLIPSOMETER OR THE LIKE SYSTEMS

(75) Inventors: Martin M. Liphardt, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 531 days.

(21) Appl. No.: 12/584,795

(22) Filed: Sep. 12, 2009

Related U.S. Application Data

(60) Provisional application No. 61/191,988, filed on Sep. 15, 2008.

(51) Int. Cl.
- *G01J 4/00* (2006.01)
- *G01N 21/00* (2006.01)
- *G01N 21/55* (2006.01)

(52) U.S. Cl. .......................... 356/369; 356/432; 356/445

(58) Field of Classification Search .......................... None  
See application file for complete search history.

(56) References Cited

U.S. PATENT DOCUMENTS

| | | | | |
|---|---|---|---|---|
| 5,101,111 A * | 3/1992 | Kondo | ..................... | 250/559.28 |
| 5,689,333 A * | 11/1997 | Batchelder et al. | ........... | 356/301 |
| 6,909,507 B2 * | 6/2005 | Norton et al. | .................. | 356/364 |
| 7,006,221 B2 * | 2/2006 | Wolf et al. | ..................... | 356/369 |
| 7,084,973 B1 * | 8/2006 | Ingram | .......................... | 356/326 |
| 7,869,040 B1 * | 1/2011 | Kwak et al. | .................... | 356/369 |
| 2009/0231558 A1 * | 9/2009 | Dishon et al. | .................... | 355/27 |
| 2010/0110427 A1 * | 5/2010 | Amary et al. | .................. | 356/302 |

FOREIGN PATENT DOCUMENTS

EP     1947445     7/2008

* cited by examiner

*Primary Examiner* — Gordon Stock, Jr.  
(74) *Attorney, Agent, or Firm* — James D. Welch

(57) ABSTRACT

A system for and method of allowing visual observation of a sample being subject to investigation by an electromagnetic beam, to identify where thereupon a beam of sample investigating electromagnetic radiation is caused to impinge, in combination with a data detector of the beam of sample investigating electromagnetic radiation after it interacts with the sample.

16 Claims, 5 Drawing Sheets

TO CONTROL OF
ELLIPSOMETER/
POLARIMETER
ELEMENT
OPERATION

VIEW-FINDER IN ELLIPSOMETER OR THE LIKE SYSTEMS

This application Claims Benefit of Provisional No. 61/191,988 Filed Sep. 15, 2008.

TECHNICAL FIELD

The present invention relates to ellipsometer, polarimeter, reflectometer and spectrophotometer or the like systems, and more particularly to a means for, and method of allowing visual observation of a sample surface being subject to investigation, to identify where thereupon a beam of sample investigating electromagnetic radiation is caused to impinge.

BACKGROUND

It is known to cause a beam of electromagnetic radiation to impinge on and interact with a sample, then analyze the effect said interaction of said beam with said sample has on said beam, to arrive at sample characterizing data. At times a sample has distinguishable regions which are to be evaluated separately, and in that case it is necessary to know where upon said sample the electromagnetic beam is actually impinging. This can be accomplished by providing a means for allowing visual observation of a sample surface. A typical approach to this is to provide a beam which approaches the sample along a substantial normal thereto. This approach works to provide a view of the sample, but can not be applied to show where an beam of electromagnetic radiation directed toward said sample at an oblique angle of incidence impinges thereupon. To achieve that result a camera must be oriented along the path of the beam oblique angle of incidence. The reason for this is that the view of the sample is based upon interception of electromagnetic radiation scattered from the sample, and where a camera is positioned above a sample with a smooth surface, very little scattering theretoward occurs, whereas far more dectectable electromagnetic radiation is available along the locus of the beam.

PCT (PCT/EP2008/087217 WO), and EPO (No. EP 947 445 A1), Patent Applications by Horiba Jobin Yvon are disclosed as they disclose using a beam splitter ahead of a data detector, which beam splitter directs sample illuminating electromagnetic radiation directed theretoward into a visualization device, while passing a sample investigation electromagnetic radiation beam into a data detector. A drawback of this approach is that some sample investigation electromagnetic radiation is diverted from the data detector, thereby reducing intensity of the sample investigating beam available to the data detector.

The present invention provides a convenient to use system and method for enabling such visual observation capability, that allows avoiding decreasing the intensity of the sample investigation beam arriving at a data detector while allowing the ability to provide illuminating electromagnetic radiation to a visualization device.

DISCLOSURE OF THE INVENTION

The present invention is a sample viewing and investigation system comprising a sequence of elements:
  a source of a beam of sample investigating electromagnetic radiation;
  a first focusing means;
  a sample supporting stage;
  a second focusing means; and
  a data detector;
and further comprising additional elements:
  optional, but preferred, light emitting diodes;
  a beam directing means; and
  a camera-display system.

In use said system enables sample investigation by directing a beam of electromagnetic radiation from said source to pass through said first focusing means, interact with a sample on said sample supporting stage, reflect therefrom, pass through said second focusing means and enter said data detector which produces sample characterizing data therefrom. Further, the positioning and use of the beam directing means, in combination with presence of ambient room light, or light from the optional light emitting diodes which light illuminates the sample, allows visual positioning of the sample with respect to where a focused beam of sample investigating electromagnetic radiation interacts therewith. Once the focused beam position on the sample is identified, the preferred present invention method then provides that the beam directing means be removed from the path of the focused beam of sample investigating electromagnetic radiation, followed by performing investigation of the sample with said focused beam of electromagnetic radiation. The purpose of the present invention is then to allow identification of the location on a sample at which a focused beam of electromagnetism, which is applied to investigate the sample, impinges.

It is noted that the beam directing means is preferably a prism which directs electromagnetic radiation directed theretoward to the sample via total internal reflection, or can be some other electromagnetic radiation directing means, such as a beam splitter. Where an electromagnetic radiation directing means will not pass a sample investigating beam of electromagnetic radiation to a data detector, (eg. a total internally reflecting prism), said electromagnetic radiation directing means must be removed during collection of a beam of sample investigating electromagnetic radiation, after it interacts with a sample, by a data detector. However, if a beam splitter is used as an electromagnetic radiation directing means, it can be left in place during collection of a beam of sample investigating electromagnetic radiation by a data detector, after it interacts with a sample. While leaving the beam splitter in place is possible, it is not preferred in the present invention as it diverts sample investigating beam intensity from a data detector.

Said sample viewing and investigation system can further comprise an aperture comprising a hole in a plate, said aperture being positioned between said source of a beam of sample investigating electromagnetic radiation and said sample. In use sample investigating electromagnetic radiation passes through said hole and ambient room light, or light from the optional light emitting diodes, is substantially co-axially therewith, scattered from the plate of said aperture. In use, the sample location is set with said beam directing means positioned between said second focusing means and data detector. Ambient light, or light from the optional light emitting diodes is applied to cause camera-display system wavelength range detectable light to scatter from the plate of said aperture and proceed toward, and interact with said sample surface, then via said beam directing means, enter the camera-display system. Once the position on the sample at which the focused beam impinges is identified, said beam directing means can be removed from the position between said second focusing means and data detector and said source of a beam of sample investigating electromagnetic radiation caused to direct an electromagnetic beam through said first focusing means, impinge on a sample, interact with said sample, pass through a second focusing means, and enter a data detector which produces sample characterizing data therefrom. Note, as mentioned above, where the beam directing means is a total internal reflection prism it must be removed during collection of sample investigating by said data detector, however, where the beam directing means is a beam splitter, said removal is optional, but preferred in the present invention.

The sample viewing and investigation system can further comprise polarization state generation means between said source and sample and a polarization state detection means between said sample and data detector to form an ellipsometer or polarimeter.

It is noted that the beam directing means can be moved manually or by a motor. Where the motor is used it can be provided a signal that indicates when accumulation of sample investigation data begins, and that signal can be used to automatically cause removal of the beam directing means from the path of the sample investigating electromagnetic radiation, thereby providing increased intensity to the data detector.

It is further noted that if the beam directing means is replaced with a beam splitter which is not removed during application of Sample investigation electromagnetic radiation, the camera-display system detectable wavelength range light provided by the light emitting diodes, if used, can be turned-off to avoid interfering with the sample investigation.

It is also note that focusing means can be any functional elements, (eg. refractive or reflective focusing elements).

A method of viewing and investigating a sample comprises:

a) providing a sample viewing and investigation system as described above:

b) while viewing said sample by causing said beam directing means to be positioned between said second focusing means and data detector and while optionally applying light emitting diodes to cause camera-display system detectable wavelength range light to proceed toward, and interact with said sample surface and via said beam directing means enter the camera-display system to form a visible display, moving the sample into a desired position;

c) preferably removing said beam directing means from the position between said second focusing means and data detector and causing said source of a beam of sample investigating electromagnetic radiation to direct an electromagnetic beam through said first focusing means, impinge on a sample supported by said sample supporting stage, then interact with said sample, pass through a second focusing means, and enter a data detector which produces sample characterizing data therefrom;

d) analyzing data provided by said data detector.

Said method can more particularly provide that said sample viewing and investigation system provided in step a specifically comprises:

an aperture comprising a plate, with hole therein, said aperture being positioned between said source of a beam of sample investigating electromagnetic radiation and said sample, such that in use sample investigating electromagnetic radiation passes through said hole, and light from the optional light emitting diodes is, substantially co-axially therewith, scattered from the plate of said aperture.

In use the sample location is, again, set with said beam directing means positioned between said second focusing means and data detector, while the optional light emitting diodes are applied cause camera-display system detectable wavelength range light to scatter from the plate of said aperture which comprises a hole in said plate, and which is positioned between said source of a beam of sample investigating electromagnetic radiation and said sample. Said scattered electromagnetic radiation proceeds toward, and interacts with said sample surface, and via said beam directing means, enter the camera-display system. Once the sample position at which the beam of sample investigating electromagnetic radiation impinges is identified as described, said beam directing means is preferably removed from the position between said second focusing means and data detector, and said source of a beam of sample investigating electromagnetic radiation is caused to direct an electromagnetic beam through said first focusing means, impinge on a sample supported by said sample supporting stage, then interact with said sample, pass through said second focusing means, and enter a data detector which produces sample characterizing data therefrom.

Again, where a beam splitter is applied as the beam directing means, said method can omit the option to remove said beam directing means in step c. Further, where a beam splitter is applied as the beam directing means, a non-preferred method can involve, along with not removing said beam directing means in step c, turning off any camera-display system detectable wavelength range light provided by the light emitting diodes during practice of step c.

A more detailed method of viewing and investigating a sample comprises:

a) providing a sample viewing and investigation system comprising a sequence of elements:

a source of a beam of sample investigating electromagnetic radiation;
an aperture comprising a plate with a hole therein;
a first focusing means;
a sample supporting stage;
a second focusing means; and
a data detector;

and further comprising additional elements:
light emitting diodes;
a beam directing means comprising a prism for causing total internal reflection therewithin of electromagnetic radiation entered thereinto; and
a camera-display system.

In use a sample can be investigated by causing a beam of electromagnetic radiation from said source to pass through the hole in said aperture and said first focusing means and become a focused beam, then reflect from a sample on said sample supporting stage, pass through said second focusing means and enter said data detector which produces sample characterizing data therefrom. Also in use, the light emitting diodes are positioned and operated to direct electromagnetic radiation toward said aperture such that it scatters therefrom and illuminates said sample, and such that the positioning of the beam directing means in combination with the camera-display system for detecting light from the light emitting diodes, allows visual positioning of the sample with respect to where the focused beam of sample investigating electromagnetic radiation interacts therewith.

Said method further comprises:

b) while causing a focused beam of sample investigating electromagnetic radiation to impinge on said sample and reflect therefrom, and while the light emitting diodes are applied to cause camera-display system detectable wavelength range light to proceed toward and scatter from said aperture and onto said sample; viewing said sample by causing said beam directing means to be moved to a position between said second focusing means and data detector, such that said beam directing means directs, via total internal reflection therewithin, electromagnetic radiation reflecting from said sample to enter the camera-display system to form a visible display;

c) moving the sample into a desired position;

d) removing said beam directing means from between said second focusing means and data detector and causing said source of a beam of sample investigating electromagnetic radiation to direct an electromagnetic beam through said hole in said aperture and first focusing means, impinge on a sample supported by said sample supporting stage, then reflect from said sample, pass through a second focusing means, and enter said data detector such that sample characterizing data is produced thereby.

Said more detailed method can involve, in step d, disabling the light emitting diodes so they are not applied to cause camera-display system detectable wavelength range light to proceed toward and reflect from said sample. And, said sample viewing and investigation system can further comprise polarization state generation and polarization state analyzer means, before and after the sample respectively, and be an ellipsometer or polarimeter.

Further, said more detailed method can involve the movement of said beam directing means practiced in steps b and d, being achieved by a selection from the group consisting of:
the beam directing means is moved manually; and
the beam directing means is moved by a motor.

It is also beneficial to include a switch in the system such that accumulation of sample characterizing data by said data detector in step d, begins only after removal of the beam directing means from the path of the sample investigating electromagnetic radiation, which removal operates said switch. This prevents data from being accumulated which is erroneous as a result of interaction with unintended elements.

The disclosed present invention methodology can also include performing at least one selection from the group consisting of:
storing at least some data provided by said data detector in machine readable media;
analyzing at least some of the data provided by said data detector and storing at least some of the results of said analysis in machine readable media;
displaying at least some data provided by said data detector by electronic and/or non-electronic means;
analyzing at least some of the data provided by said data detector and displaying at least some of the results of said analysis by electronic and/or non-electronic means;
causing at least some data provided by said data detector to produce a signal which is applied to provide a concrete and tangible result; and
analyzing at least some of the data provided by said data detector and causing at least some thereof to produce a signal which is applied to provide a concrete and tangible result.

The present invention will be better understood by reference to the Detailed Description Section of this Specification, with reference to the Drawings.

DETAILED DESCRIPTION

Figure 6:
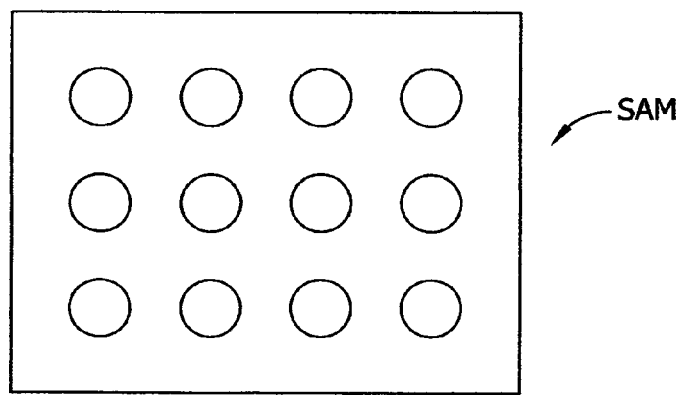
FIG. 6 shows a Sample (SAM) with a plurality of regions which can be investigated individually.

Turning now to Figures, it is convenient to first note that FIG. 6 shows a sample with a plurality of distinguishable regions present on the surface thereof, each of which might be individually investigated.

Figure 1:
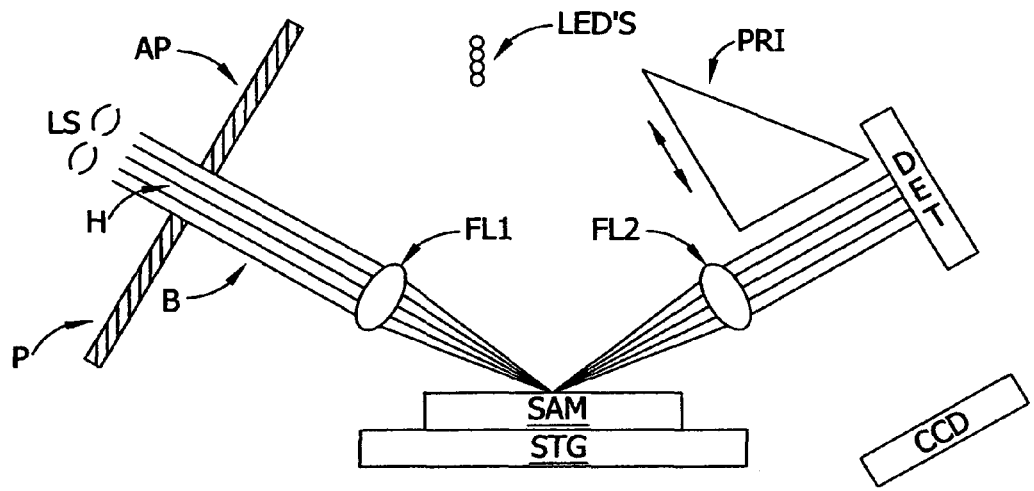
FIG. 1 shows a present invention system configured to investigate a Sample (SAM) using an oblique angle of incidence Beam of Electromagnetic Radiation which reflects from said Sample (SAM).
Figure 8:
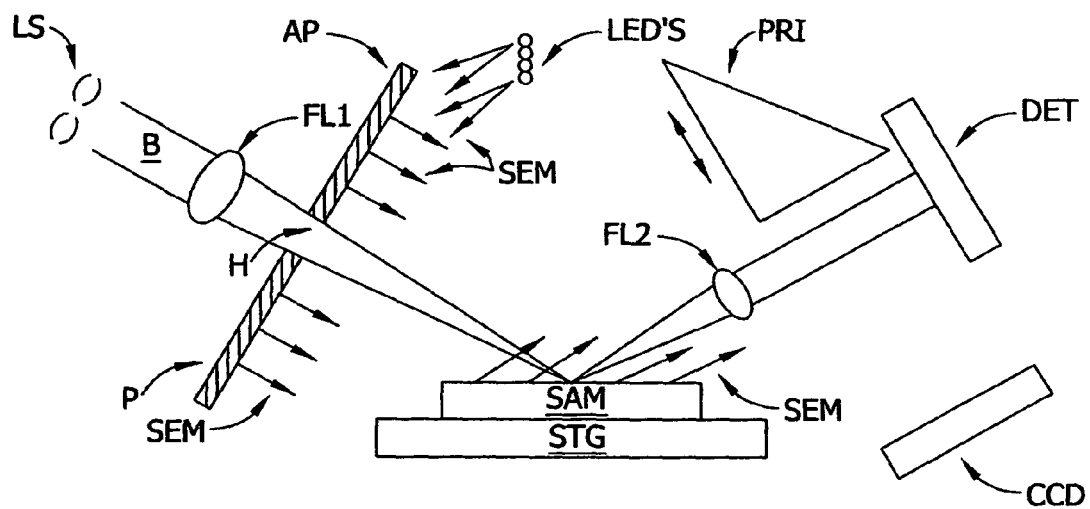
FIG. 8 shows a modified FIG. 1 with the Aperture (AP) moved to a position between the Focusing Lens (FL1) and Sample (SAM).

FIG. 1 shows that a Source (LS) of a Beam (B) of Sample Investigating Electromagnetic radiation is caused to direct said Beam (B) to become focused by passing through a First Focusing Means (FL1), impinge on a Sample (SAM) at an oblique angle of incidence, then reflect from said Sample (SAM), pass through a Second Focusing Means (FL2), and enter a Data Detector (DET). Note the present of an Aperture (AP) comprising a hole (H) in a plate (P), Light Emitting Diodes (LED's), a Beam Directing Means (PRI) and a Camera-Display System (CCD). Note the position of the Beam Directing Means (PRI) and that it can be moved as indicated by the double directed arrow. FIG. 8 shows a modified FIG. 1 with the Aperture (AP) moved to a position between the Focusing Means (FL1) and Sample (SAM). In many instances the FIG. 8 configuration is preferred.

Figure 2:
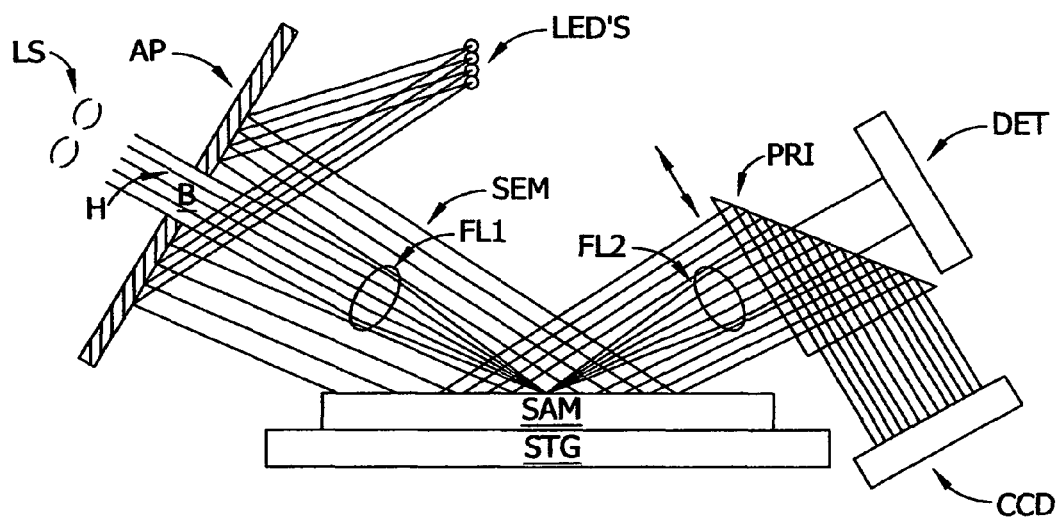
FIG. 2 shows a present invention system as in FIG. 1, configured view a Sample (SAM).

FIG. 2 shows FIG. 1 with the Beam Directing Means (PRI) moved into a position between the Second Focusing Means (FL2) and Data Detector (DET). In use the Light Emitting Diodes (LED's) are shown applied to cause Camera-Display System (CCD) detectable wavelength range light to scatter from the Aperture (AP), proceed toward and reflect from said Sample (SAM) surface, and via said Beam Directing Means (PRI) which is entered into the position shown, enter the Camera-Display System (CCD). Note that, when used, light from the Light Emitting Diodes (LED's) is scattered from the Aperture (AP) Plate (P) as Scattered Electromagnetic Radiation (SEM). This is to avoid point source light from the Light Emitting Diodes (LED's) arriving at the Camera-Display System (CCD) and complicating a visual observation of the Sample (SAM) surface. In some cases room ambient light can be sufficient and light from the Light Emitting Diodes (LED's) is not necessary.

In use, the FIG. 2 arrangement is applied to allow a user to visually identify where upon a Sample (SAM) surface the Electromagnetic Beam (B) provided by the Source thereof (LS) will be focused. Then the Beam Directing Means (PRI) can be, but is not necessarily moved to the position as shown in FIG. 1 and said Electromagnetic Beam (B) caused to become focused, interact with said Sample (SAM) at a known location on the surface thereof, reflect therefrom, be collected by the Second Focusing Means (FL2) and enter the Data Detector (DET). Analysis of Data Detector (DET) output allows Sample (SAM) characterization such as determination of optical constants and film thicknesses etc.

Figure 3:
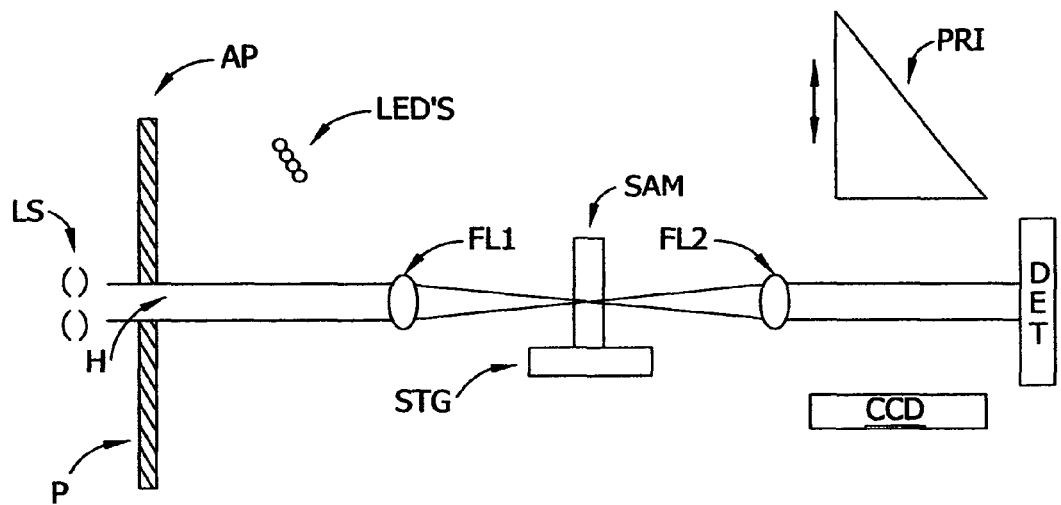
FIG. 3 shows a present invention system configured to investigate a Sample (SAM) using a normal angle of incidence Beam of Electromagnetic Radiation which transmits through said Sample (SAM).
Figure 4:
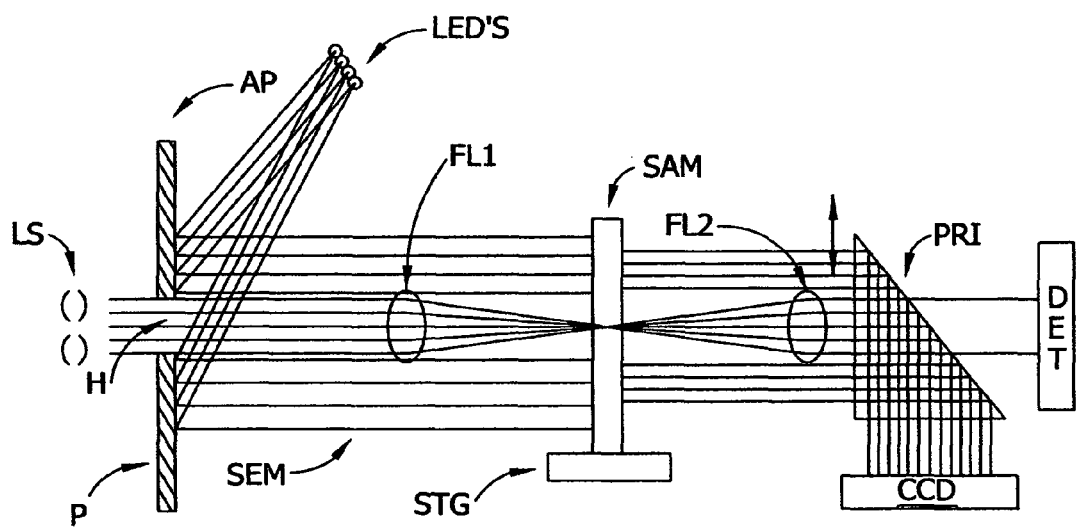
FIG. 4 shows a present invention system as in FIG. 3, configured view a Sample (SAM).
Figure 5:
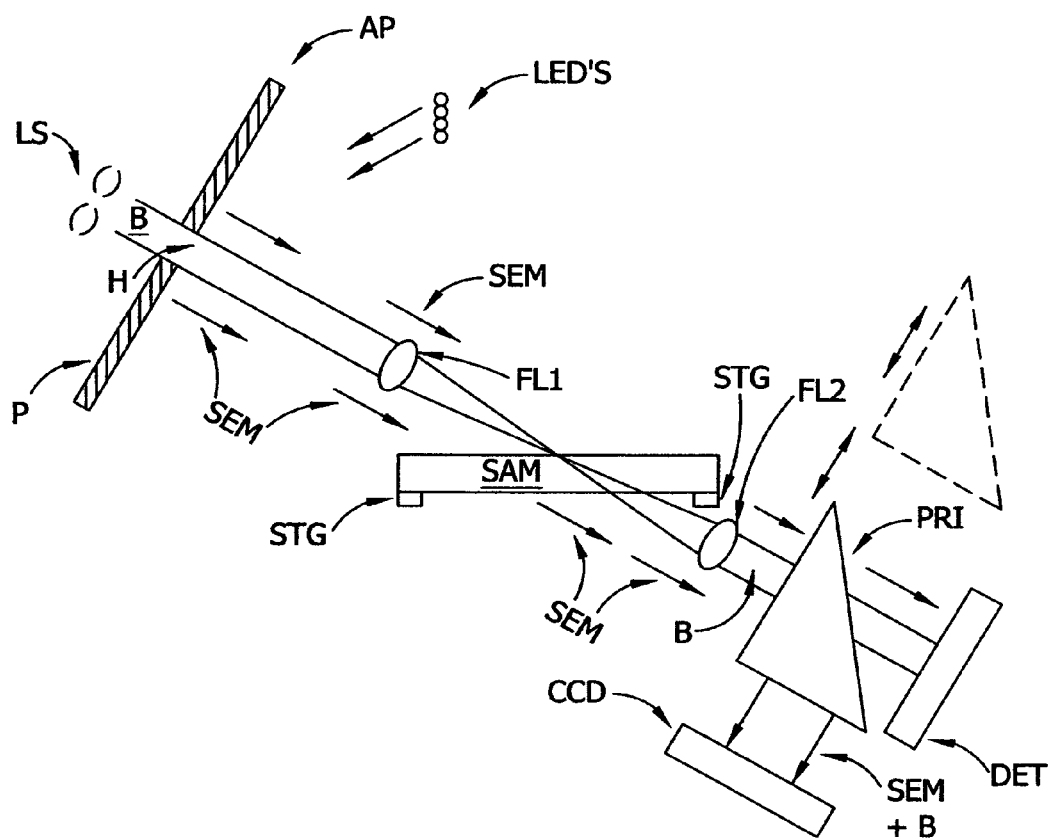
FIG. 5 shows a present invention system configured to investigate a Sample (SAM) using an oblique angle of incidence Beam of Electromagnetic Radiation which transmits through said Sample (SAM).

FIGS. 3 and 4 are analogically similar to FIGS. 1 and 2, respectively, but with the overall system configured to allow Sample (SAM) investigation by a focused Electromagnetic Beam (B) which approaches the Sample (SAM) along a normal to the surface thereof and transmits therethrough then enters the Data Detector (DET). FIG. 5 shows that a transmission mode investigation of the Sample (SAM) can also be pursued where a focused Electromagnetic Beam (B) approaches the Sample (SAM) at an oblique angle of incidence.

In all configurations, it is to be appreciated that the positioning and use of the Beam Directing Means (PRI), in combination with use of scattered light from the Light Emitting Diodes (LED's) to allow, in use, visual positioning of the Sample (SAM) prior to optionally removing the Beam Directing Means (PRI) and performing investigation of the Sample (SAM) with the Focused Beam (B), is the focal aspect of the invention.

Figure 7:
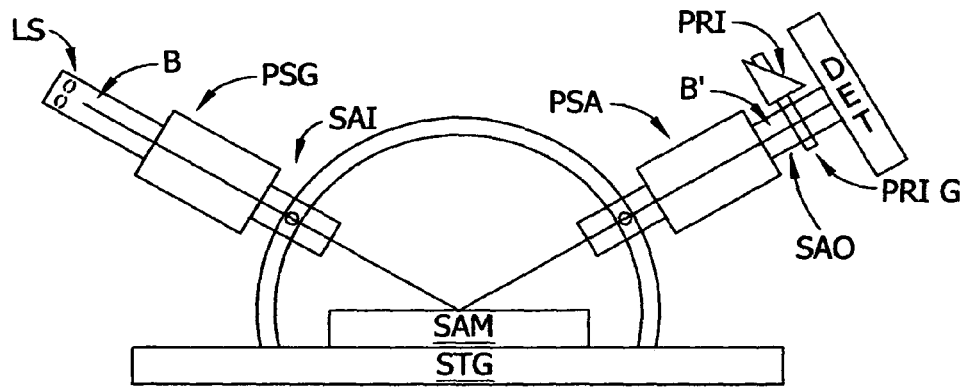
FIG. 7 shows the elements of an Ellipsometer or Polarimeter.

As application of the present invention is particularly well suited for use in Ellipsometers and Polarimeters, FIG. 7 is included to show the basic elements of an Ellipsometer or Polarimeter. Note the presence of a Polarization State Generator (PSG) which serves to set a state of polarization in a Beam (B) of Electromagnetic Radiation provided by the Source (LS) thereof. Accompanying is a Polarization State Analyzer (PSA) for determining a change in polarization state caused by interaction with he Sample (SAM). When polarization state is not controlled by application of a (PSG), the system is a Reflectometer or Spectrophotometer. Also note the presence of Arms (SAI) and (SAO) which support the (LS) (PSG) and the (PSA) (DET) respectively. Also note the presence of a Guide (PRIG) for enabling movement of the Beam Directing Means (PRI) into and out of a Beam (B') before it enters the Data Detector (DET). This is a demonstrative, and not limiting, system for effecting the desired result.

It is noted that the Second Focusing Means (FL2) is actually applied to re-collimate a focused beam after it reflects from a Sample (SAM).

Figure 9:
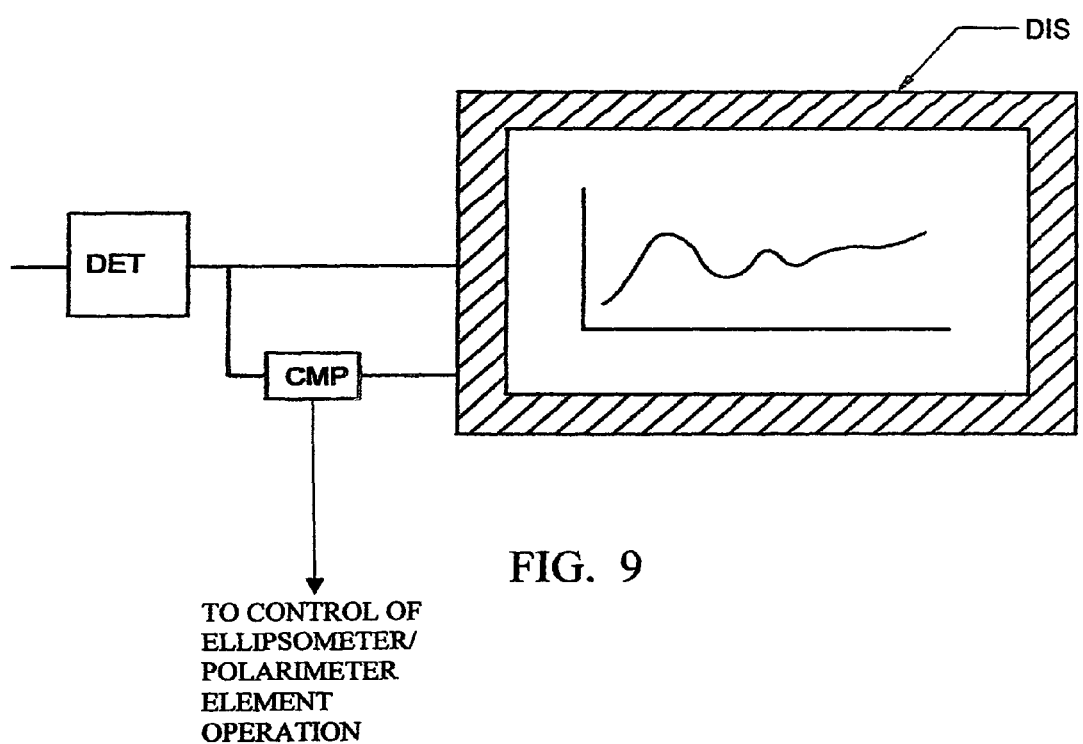
FIG. 9 is included to show that a present invention system can be controlled by a computer.

FIG. 9 is included to show that operation of a present invention system can be controlled by a Computer (CMP). Further, data provided by the Data Detector (DET), or analyzed results thereof, can be presented in a Display (DIS).

Finally, the Drawings show the Beam Directing Means (PRI) as a Prism for providing a Total Internal Reflecting surface at the hypotenuse, opposite the 90 degree angle, of the triangular shape as viewed in side elevation. It is to be understood that this is preferred, however, the legs of the shown triangular shape can be eliminated and the remaining hypotenuse can represent a Beam Splitter which partially reflects and partially transmits a beam of electromagnetic radiation cause to impinge thereupon at an oblique angle of incidence. The Drawings and Claims are to be so interpreted where appropriate.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of viewing and investigating a sample (SAM) comprising:
   a) providing a sample viewing and investigation system comprising a sequence of elements:
      a source (LS) of a beam (B) of sample investigating electromagnetic radiation;
      an aperture (AP) comprising a plate (P), with a hole (H) therein;
      a first focusing means (FL1);
      a sample supporting stage (STG);
      a second focusing means (FL2); and
      a data detector (DET);
   and further comprising additional elements:
      light emitting diodes (LED's);
      a beam directing means (PRI) comprising a prism for causing total internal reflection therewithin of electromagnetic radiation entered thereinto; and
      a camera-display system (CCD);
   such that in use a sample (SAM) can be investigated by causing a beam (B) of electromagnetic radiation from said source (LS) to pass through the hole (H) in said aperture (AP) and said first focusing means and become a focused beam, then reflect from the sample (SAM) on said sample supporting stage (STG), pass through said second focusing means (FL2) and enter said data detector (DET) which produces sample characterizing data therefrom; and
   such that, in use, the light emitting diodes (LED's) are positioned on a sample side of the aperture and operated to direct electromagnetic radiation toward said aperture (AP), such that said electromagnetic radiation scatters therefrom and illuminates said sample (SAM), and such that a positioning of the beam directing means (PRI) in combination with the camera-display system (CCD) for detecting light from the light emitting diodes (LED's), allows visual positioning of the sample (SAM) with respect to where the focused beam of sample investigating electromagnetic radiation interacts therewith;
   b) while causing a focused beam of sample investigating electromagnetic radiation to impinge on said sample (SAM) and reflect therefrom, and while the light emitting diodes (LED's) are applied to cause camera-display system (CCD) detectable wavelength range light to proceed toward and scatter from said aperture (AP) and onto said sample (SAM); viewing said sample by causing said beam directing means (PRI) to be moved to a position between said second focusing means (FL2) and data detector (DET), such that said beam directing means (PRI) directs, via total internal reflection therewithin, electromagnetic radiation reflecting from said sample (SAM) to enter the camera-display system (CCD) to form a visible display;
   c) moving the sample (SAM) into a desired position;
   d) removing said beam directing means (PRI) from between said second focusing means (FL2) and data detector (DET) and causing said source (LS) of a beam (B) of sample investigating electromagnetic radiation to direct an electromagnetic beam (B) through said hole (H) in said aperture (AP) and first focusing means (FL1), impinge on the sample (SAM) supported by said sample supporting stage (STG), then reflect from said sample (SAM), pass through the second focusing means (FL2), and enter said data detector (DET) such that sample characterizing data is produced thereby.

2. A method as in claim 1, in which the light emitting diodes (LED's) are not applied to cause camera-display system (CCD) detectable wavelength range light to proceed toward and reflect from said sample (SAM) during the step d data detector (DET) production of sample characterizing data.

3. A method as in claim 1 wherein the sample viewing and investigation system further comprises a polarization state generation means (PSG) between said source (LS) and sample (SAM) and wherein the sample viewing and investigation system is an ellipsometer or polarimeter.

4. A method as in claim 1 that further comprises:
 e) performing at least one selection from the group consisting of:
  storing at least some data provided by said data detector (DET) in machine readable media;
  analyzing at least some data provided by said data detector (DET) and storing at least some results of said analysis in machine readable media;
  displaying at least some data provided by said data detector (DET);
  analyzing at least some data provided by said data detector (DET) mid displaying at least some results of said analysis;
  causing at least some data provided by said data detector (DET) to produce a signal which is applied to provide a physical result;
  analyzing at least some data provided by said data detector (DET) and causing at least some thereof to produce a signal which is applied to provide a physical result.

5. A method as in claim 1 wherein movement of said beam directing means (PRI) practiced in steps b and d, is achieved by a selection from the group consisting of:
 the beam directing means (PRI) is moved manually; and
 the beam directing means (PRI) is moved by a motor.

6. A method as in claim 5, in which the sample viewing and investigation system further comprises a switch, operation of which enables accumulation of sample characterizing data by said data detector (DET) in step d, only after removal of the beam directing means (PRI) from a path of the sample (SAM) investigating electromagnetic radiation.

7. A sample viewing and investigation system comprising a sequence of elements:
 a source (LS) of a beam (B) of sample investigating electromagnetic radiation;
 a first focusing means (FL1);
 a sample supporting stage (STG);
 a second focusing means (FL2); and
 a data detector (DET);
and further comprising additional elements:
 light emitting diodes (LED's);
 a beam directing means (PRI); and
 a camera-display system (CCD);
such that in use a sample can be investigated by causing a beam (B) of electromagnetic radiation from said source (LS) to pass through said first focusing means and become focused, then reflect from the sample (SAM) on said sample supporting stage (STG), pass through said second focusing means (FL2) and enter said data detector (DET) which produces sample characterizing data therefrom; and
such that, in use, a positioning of the beam directing means (PRI) in combination with the camera-display system (CCD) for detecting room ambient light or light from the light emitting diodes (LED's), allows visual positioning of the sample (SAM) with respect to where the focused beam (B) of sample investigating electromagnetic radiation interacts therewith prior to performing investigation of the sample (SAM) with said focused beam (B); wherein the sample viewing and investigation system further comprises an aperture (AP) comprising a hole (H) in a plate (P), said aperture (AP) being positioned between said source (LS) of a beam (B) of sample investigating electromagnetic radiation and said sample (SAM), such that in use sample (SAM) investigating electromagnetic radiation passes through said hole (H), and said camera-display system (CCD) detectable room ambient light or light from the light emitting diodes (LED's) is, substantially co-axially therewith, scattered from the plate of said aperture (AP); wherein, when the light of the light emitting diodes (LED's) is detected, the light of the light emitting diodes is applied to a sample side of the aperture.

8. A sample viewing and investigation system as in claim 7 wherein, the light of the light emitting diodes (LED's) is detected, in use, the sample (SAM) position is set with said beam directing means (PRI) positioned between said second focusing means (FL2) and data detector (DET), while the light emitting diodes (LED's) are applied to the sample side of the aperture camera-display system (CCD) detectable wavelength range light to scatter from the plate (P) of said aperture (AP), which is positioned between said source (LS) of a beam (B) of sample investigating electromagnetic radiation and said sample (SAM), as scattered electromagnetic radiation (SEM) such that said scattered electromagnetic radiation (SEM) proceeds toward, and interacts with said sample (SAM), and via said beam directing means (PRI), enters the camera-display system (CCD);
and such that once the sample (SAM) position is identified as described, said beam directing means (PRI) is subjected to a selection from the group consisting of:
 being removed from; and
 not being removed from
between said second focusing means (FL2) and data detector (DET), and said source (LS) of a beam (B) of sample investigating electromagnetic radiation is caused to direct an electromagnetic beam (B) through said first focusing means (FL1), impinge on the sample (SAM) supported by said sample supporting stage (STG), then interact with said sample (SAM), pass through the second focusing means (FL2), and enter the data detector (DET) which produces sample characterizing data therefrom.

9. A sample viewing and investigation system as in claim 7, which further comprises polarization state generation means (PSG) between said source (LS) and sample (SAM) and wherein the sample viewing and investigation system is an ellipsometer or polarimeter.

10. A method of viewing and investigating a sample (SAM) comprising:
 a) providing a sample viewing and investigation system comprising a sequence of elements:
  a source (LS) of a beam (B) of sample investigating electromagnetic radiation;
  a first focusing means (FL1);
  a sample supporting stage (STG);
  a second focusing means (FL2); and
  a data detector (DET);
 and further comprising additional elements:
  light emitting diodes (LED's);
  a beam directing means (PRI); and
  a camera-display system (CCD);
such that in use a sample can be investigated by causing a beam (B) of electromagnetic radiation from said source (LS) to pass through said first focusing means and become focused, then interact with the sample (SAM) on said sample supporting stage (STG), reflect therefrom, pass through said second focusing means (FL2) and enter said data detector (DET) which produces sample characterizing data therefrom; and
 such that, in use, a positioning of the beam directing means (PRI) in combination with the camera-display system (CCD) for detecting room ambient light or light from the light emitting diodes (LED's), allows visual positioning of the sample (SAM) with respect to where the focused beam (B) of sample investigating electromagnetic radiation interacts therewith prior to performing investigation of the sample (SAM) with said focused beam (B);

b) viewing said sample by causing said beam directing means (PRI) to be positioned manually or by a motor between said second focusing means (FL2) and data detector (DET), while the room ambient light or light emitting diodes (LED's) is applied to cause camera-display system (CCD) detectable wavelength range light to proceed toward, and interact with said sample (SAM), and via said beam directing means (PRI), enter the camera-display system (CCD) to form a visible display, and moving the sample (SAM) into a desired position;

c) after said viewing, removing said beam directing means (PRI) manually or by the motor (PRI) from between said second focusing means (FL2) and data detector (DET) and causing said source (LS) of a beam (B) of sample investigating electromagnetic radiation to direct an electromagnetic beam (B) through said first focusing means (FL1), impinge on the sample (SAM) supported by said sample supporting stage (STG), then interact with said sample (SAM), pass through the second focusing means (FL2), and enter the data detector (DET) which produces sample characterizing data therefrom.

11. A method as in claim 10 wherein the provided sample viewing and investigation system further comprises:

an aperture (AP) comprising a plate (P), with a hole (H) therein, said aperture (AP) being positioned between said source (LS) of a beam (B) of sample investigating electromagnetic radiation and said sample (SAM), such that in use sample (SAM) investigating electromagnetic radiation passes through said hole (H), and room ambient light or light from the light emitting diodes (LED's) is, co-axially therewith, scattered from the plate (P) of said aperture (AP);

such that in use the sample (SAM) position is set with said beam directing means (PRI) positioned between said second focusing means (FL2) and, data detector (DET), while room ambient light or the light from the light emitting diodes (LED's) is applied to cause camera-display system (CCD) detectable wavelength range light to scatter from the plate (P) of said aperture (AP) which comprises the hole (H) in said plate (P), which is positioned between said source (LS) of a beam (B) of sample investigating electromagnetic radiation and said sample (SAM), as scattered electromagnetic radiation (SEM) such that said scattered electromagnetic radiation (SEM) proceeds toward, and interacts with said sample (SAM), and via said beam directing means (PRI), enter the camera-display system (CCD);

and such that once the sample (SAM) position is identified as described, said beam directing means (PRI) can be removed from between said second focusing means (FL2) and data detector (DET) and said source (LS) of a beam (B) of sample investigating electromagnetic radiation is caused to direct an electromagnetic beam (B) through said first focusing means (FL1), impinge on the sample (SAM) supported by said sample supporting stage (STG), then interact with said sample (SAM), pass through said second focusing means (FL2), and enter the data detector (DET) which produces sample characterizing data therefrom.

12. A method as in claim 10 wherein the motor is used to move the beam directing means (PRI), and said motion is initiated by a signal that indicates when accumulation of sample investigation data begins, said signal being applied to effect motor operation and automated removal of the beam directing means (PRI) from a path of the sample investigating electromagnetic radiation thereby providing a maximum of intensity to the data detector.

13. A method as in claim 10, which further comprises:

d) performing at least one selection from the group consisting of:

storing at least some data provided by said data detector (DET) in machine readable media;

analyzing at least some data provided by said data detector (DET) and storing at least some results of said analysis in machine readable media;

displaying at least some data provided by said data detector (DET);

analyzing at least some data provided by said data detector (DET) and displaying at least some results of said analysis;

causing at least some data provided by said data detector (DET) to produce a signal which is applied to provide a physical result; and analyzing at least some data provided by said data detector (DET) and causing at least some thereof to produce a signal which is applied to provide a physical result.

14. A sample viewing and investigation system comprising a sequence of elements:

a source (LS) of a beam (B) of sample investigating electromagnetic radiation;

an aperture (AP) comprising a plate (P), with a hole (H) therein;

a first focusing means (FL1);

a sample supporting stage (STG);

a second focusing means (FL2); and a data detector (DET);

and further comprising additional elements:

light emitting diodes (LED's);

a beam directing means (PRI) comprising a selection from the group:

a prism for causing total internal reflection therewithin of electromagnetic radiation entered thereinto; and a specularly reflecting mirror;

and a camera-display system (CCD);

such that in use a sample (SAM) can be investigated by causing a beam (B) of electromagnetic radiation from said source (LS) to pass through the hole (H) in said aperture (AP) and said first focusing means and become a focused beam, then reflect from the sample (SAM) on said sample supporting stage (STG), pass through said second focusing means (FL2) and enter said data detector (DET) which produces sample characterizing data therefrom; and such that, in use, the light emitting diodes (LED's) are positioned on a sample side of the aperture and operated to direct electromagnetic radiation toward said aperture (AP) such that said electromagnetic radiation scatters therefrom and illuminates said sample (SAM), and such that a positioning of the beam directing means (PRI) in combination with the camera-display system (CCD) for detecting light from the light emitting diodes (LED's), allows visual positioning of the sample (SAM) with respect to where a focused beam of sample investigating electromagnetic radiation interacts therewith.

15. A sample viewing and investigation system as in claim 14 which further comprises a polarizer between said source (LS) of a beam (B) of sample (SAM) investigating electromagnetic radiation and said sample (SAM), and an analyzer between said sample (SAM) and detector (DET), said sample viewing and investigation system being an ellipsometer or polarimeter.

16. A method of viewing and investigating a sample (SAM) comprising:
   a) providing a sample viewing and investigation system comprising a sequence of elements:
      a source (LS) of a beam (B) of sample investigating electromagnetic radiation;
      a first focusing means (FL1);
      a sample supporting stage (STG);
      a second focusing means (FL2); and
      a data detector (DET);
   and further comprising additional elements:
      a beam directing means (PRI); and
      a camera-display system (CCD);
   such that in use a sample can be investigated by causing a beam (B) of electromagnetic radiation from said source (LS) to pass through said first focusing means and become focused, then interact with the sample (SAM) on said sample supporting stage (STG), reflect therefrom, pass through said second focusing means (FL2) and enter said data detector (DET) which produces sample characterizing data therefrom; and
   such that, in use, a positioning of the beam directing means (PRI) in combination with the camera-display system (CCD) for detecting room ambient light allows visual positioning of the sample (SAM) with respect to where a focused beam (B) of sample investigating electromagnetic radiation interacts therewith prior to performing investigation of the sample (SAM) with said focused beam (B);
   b) viewing said sample by causing said beam directing means (PRI) to be positioned manually or by a motor between said second focusing means (FL2) and data detector (DET), while the room ambient light is applied to cause camera-display system (CCD) detectable wavelength range light to proceed toward, and interact with said sample (SAM), and via said beam directing means (PRI), enter the camera-display system (CCD) to form a visible display, and moving the sample (SAM) into a desired position;
   c) after said viewing, removing said beam directing means (PRI) manually or by the motor (PRI) from the position between said second focusing means (FL2) and data detector (DET) and causing said source (LS) of a beam (B) of sample investigating electromagnetic radiation to direct an electromagnetic beam (B) through said first focusing means (FL1), impinge on the sample (SAM) supported by said sample supporting stage (STG), then interact with said sample (SAM), pass through the second focusing means (FL2), and enter the data detector (DET) which produces sample characterizing data therefrom.

* * * * *